United States Patent [19]

Beakbane

[11] Plant 4,061

[45] June 14, 1977

[54] PLUM ROOTSTOCK—PIXY VARIETY

[75] Inventor: A. Beryl Beakbane, East Malling, England

[73] Assignee: National Seed Development Organisation Limited, Newton, England

[21] Appl. No.: 696,307

[22] Filed: June 15, 1976

[51] Int. Cl.[2] ..... A01H 5/03

[52] U.S. Cl. ..... Plt./38

[58] Field of Search ..... Plt./38

*Primary Examiner*—Robert E. Bagwill

*Attorney, Agent, or Firm*—Burns, Doane, Swecker & Mathis

[57] ABSTRACT

The invention relates to a new and distinct variety of plum tree which is useful as a dwarfing rootstock. Plum trees grown on the understock of this variety attain about two-thirds of the size as those on St. Julien A understock, and are more precociously bearing thereby manifesting a greater cropping efficiency. Also, hedges of this variety exhibit a more spreading habit in contrast to the vigorous upright shoots of St. Julien type rootstocks, and are resistant to bacterial canker.

6 Drawing Figures

PLUM ROOTSTOCK—PIXY VARIETY

SUMMARY OF THE INVENTION

The original plant was selected in 1971 from 1500 seedlings which germinated from seed obtained in France in 1947. The trees producing the seed were previously selected from *Prunus insititia*, St. Julien d'Orleans types. The pollen parent of the new variety is unknown. Following evaluation and testing at East Malling Research Station, Maidstone, Kent, England the new variety was found to be useful as a dwarf rootstock which is compatible with plums and gages. Further tests of peach and apricot are necessary before its compatibility with these fruits can be fully assessed. The rootstock of the present invention has been designated the Pixy variety.

Plum trees worked on the new variety are much smaller and more precociously bearing trees than those worked on St. Julien A. Heavy crops are borne early in the tree's life, and fruit thinning may be necessary in certain seasons to maintain good size on the heavy bearing trees on this understock. The cropping efficiency, i.e. crop in relation to cubic head of tree is greater on this variety, than on St. Julien A. Also, the variety shows resistance to bacterial canker.

In common with other dwarfing rootstocks this variety exhibits some signs of water stress in severe drought conditions.

Plum trees of the Pixy variety may be easily propagated by hardwood cuttings given a hormone quick dip and lined out directly into the open field. Such asexual reproductions at the East Malling Research Station have demonstrated that its distinctive characteristics including its dwarfing character are stable and are transmitted without change through succeeding propagations.

BRIEF DESCRIPTION OF THE DRAWINGS

The accompanying drawings show typical specimens of the improved rootstock wherein.

DETAILED DESCRIPTION

Figure 1:
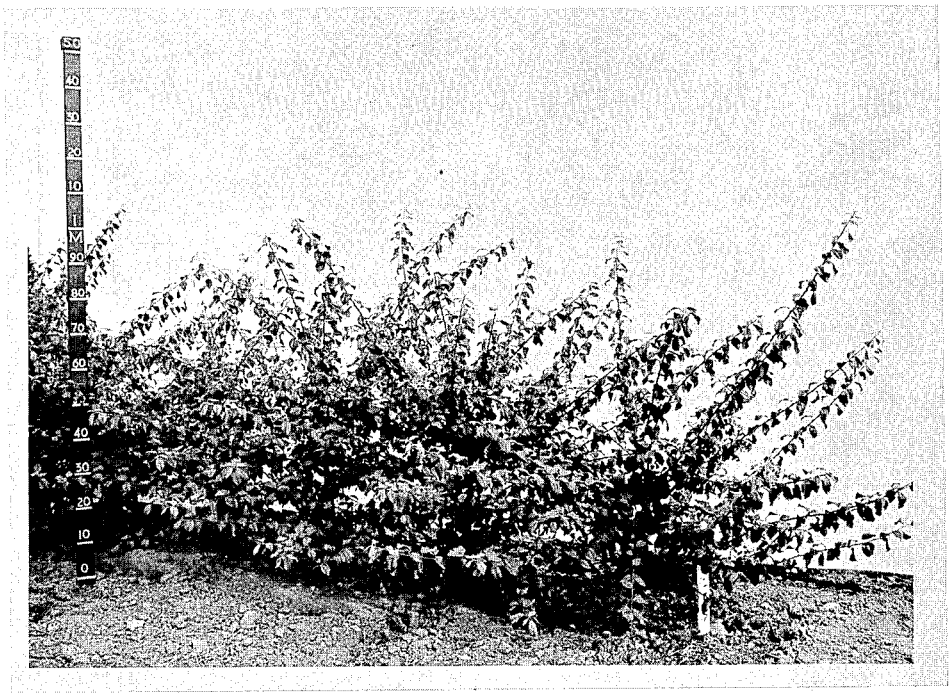
FIG. 1 is a hedge of the Pixy variety planted at the East Malling Research Station in 1973, and photographed during August, 1975 with the height being shown in centimeters.
Figure 2:
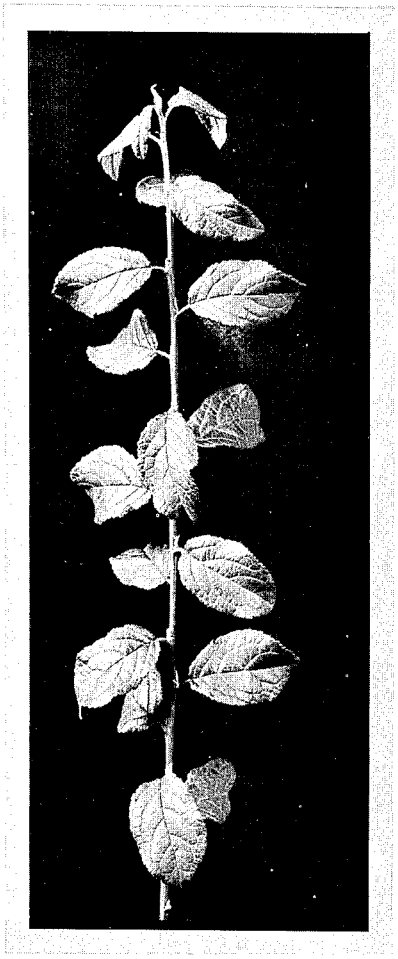
FIG. 2 is a one year old vegetative shoot of the Pixy variety grown at the East Malling Research Station.
Figure 3:
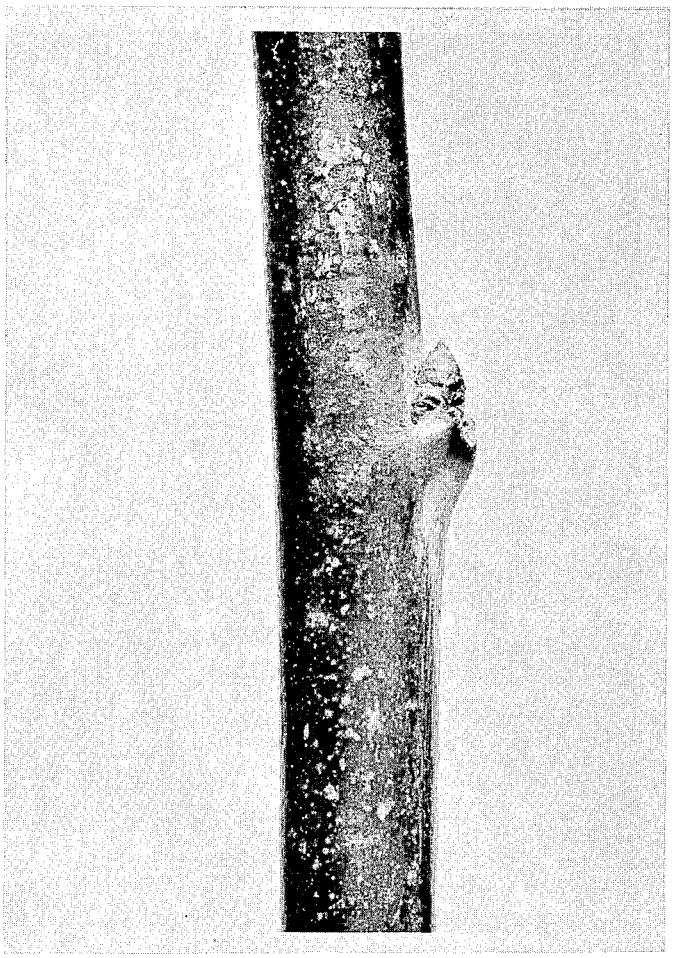
FIG. 3 is a dormant bud of the Pixy variety.
Figure 4:
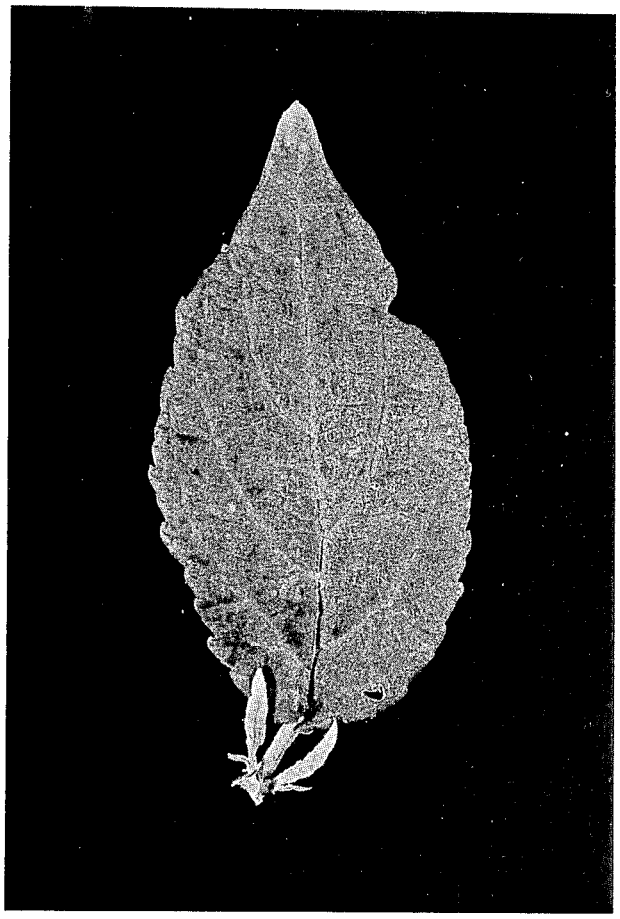
FIG. 4 is a leaf of the Pixy variety.
Figure 5:
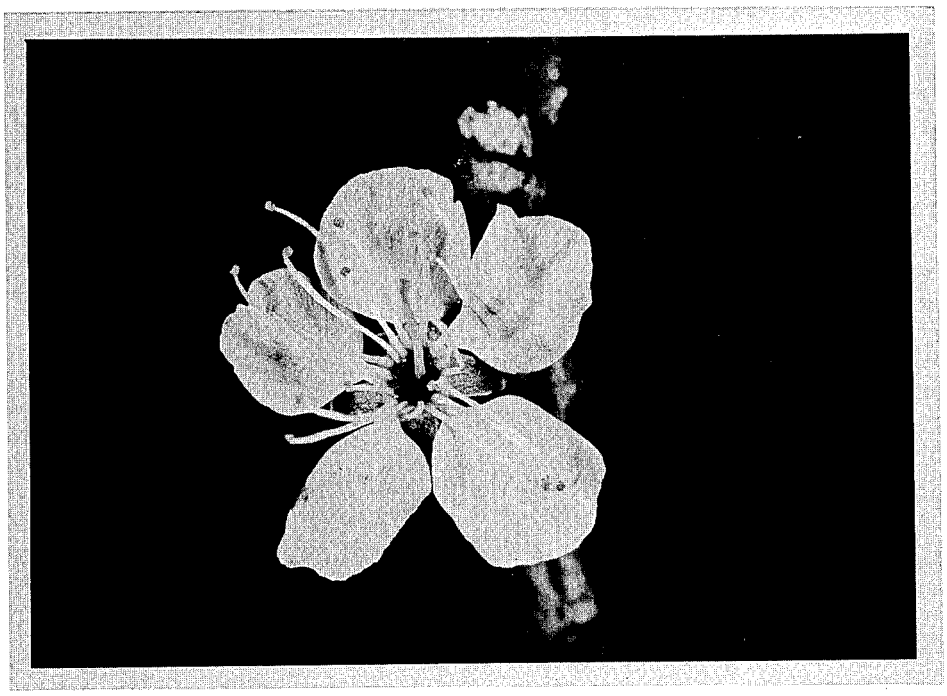
FIG. 5 is a flower of the Pixy variety.
Figure 6:
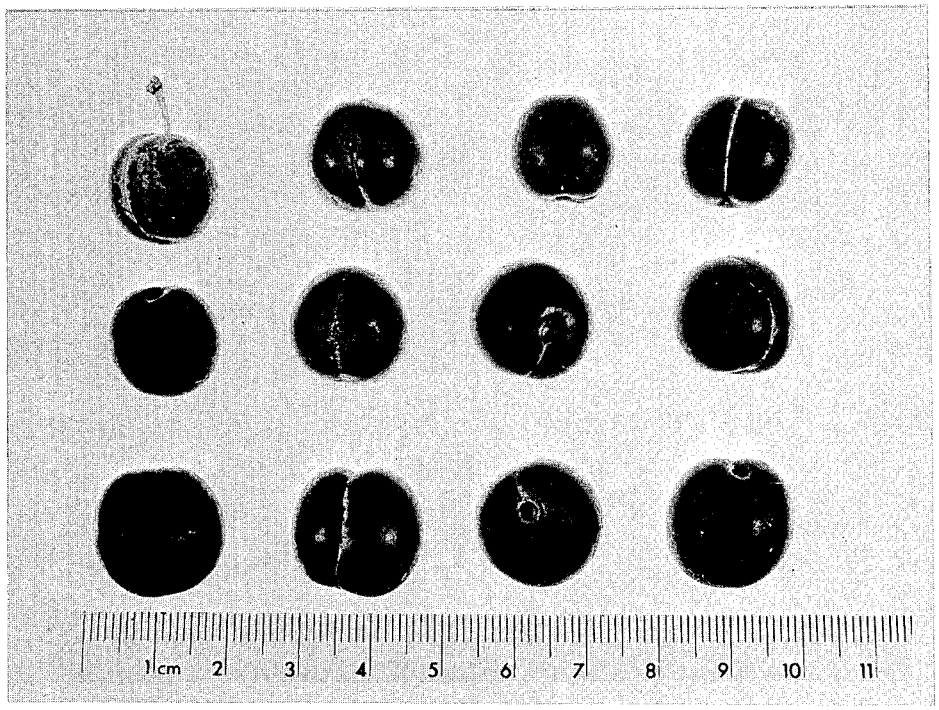
FIG. 6 is fruit of the Pixy variety.

The following is a detailed description of the new rootstock's winter and summer characters, as observed on one year old shoots produced on hedges. These characteristics are those most often seen and used in the identification of a rootstock. Colors of leaves and shoots vary with growing conditions and are not considered of value in the identification of the rootstock.

Where color assessment has been made reference is to Munsell Color Charts for Plant Tissues, 1st Edition (1952), Munsell Color Co. Inc., Baltimore, Md., U.S.A. In other instances general color terms are used in accordance with their ordinary dictionary significance.

The color description given refers to plants grown at East Malling Research Station, Kent, England.

Distinctive Points

Hedges of the Pixy variety have a spreading habit in contrast to the vigorous upright shoots of St. Julien type rootstocks. Shoots are thin and flexible, with some laterals, and are produced in moderate quantity.

The new variety has a relatively short season of growth, leafing out in late Spring and usually ceasing growth by the end of August.

General habit:

*Strength of growth.*—Moderate number thinnish flexible shoots.

*Habit.*—Spreading.

*Number of laterals.*—Few.

*Feathering on current growth.*—Some.

*Number of shoots on hedge.*—Moderate, neither sparse nor prolific, approx. the same as St. Julien A.

Wood — Summer:

*Color.*—Deep bluish-purple on upper side, green on lower side.

*Hairiness.*—Hairless.

*Texture.*—Ridged and furrowed to a greater or less extent, especially below leaf attachments.

Wood — Winter:

*Stoutness.*—Thin and slender.

*Diameter of shoots.*—Between buds: 4.01 mm; (thin) (internodal) across buds: 4.15 mm; through buds: 5.36 mm.

*Flexibility.*—Flexible.

*Internodes.*—Medium, 21.16 mm.

*Color.*—Deep bluish-purple on upper side (Munsell 5.0 RP 3/2) with slight bloom increasing towards the tip, and olive-green on the underside (2.5GY 5/4).

*Pubescence.*—One year shoots are smooth and practically hairless.

*Texture.*—Somewhat ridged in upper half of shoot.

Lenticels:

*Number.*—Numerous.

*Conspicuousness.*—Inconspicuous.

*Shape.*—Roundish.

*Color.*—Pale.

*Distribution.*—Scattered.

*Size.*—Very small.

Leaves:

*Size.*—Small, length 43.3 mm; breadth 26.8 mm; (L/B = 1.616).

*Shape.*—Ovate-elliptic.

*Base.*—Rounded.

*Apex.*—May be obtuse, but often acute or acuminate; tip may be abaxially and laterally curved.

*Serrations.*—Serrate.

*Surface.*—Not very shiny, with occasional hairs on sunken vein channels.

*Margin.*—Tending to turn under.

*Pose in relation to stem.*—Down-turned.

*Color.*—Somewhat dull green (Munsell 5 GY 5/8-6/8).

*Hairiness on under surface.*—Few hairs along veins, which are raised.

*Texture.*—Very crinkled when young, when fully expanded much smoother and flatter.

*Color of tips of shoots.*—Pale yellowish green when still actively growing.

Petiole:

*Hairs.*—Hairy.

*Shape.*—Channelled.

*Length.*—Short, 5.04 mm.

*Color.*—Green.

*Pose.*—More or less upturned, often forming an acute angle with the stem.

*Glands.*—None, one or two, usually on leaf base.

Stipules (sometimes present):

*Size.*—Long, thick Myrobalan/St. Julien A type.

*Margin.*—Hairy, entire with glandular projections.

*Shape.*—Long and narrow.

*Pose.*—Standing erect away from the shoot.

Buds:

*Size.*—Small.

*Shape.*—Plump, broad and pointed.

*Compactness.*—Compact.

*Color.*—Dark brown, waxy coating in places (Munsell 5.0 R 3/2).

*Hairiness.*—Hairless.

*Pose.*—Somewhat out-turned.

Flower and Fruit Characters

Flowers: Buds and flowers white, borne on spurs on wood more than one year old.

*Season of blossoming.*—Late March – early April over seasons 1972–1976.

Fruit: No commercial value. The suture, or arête, identifies the fruit as a St. Julien type.

*Harvest date.*—Early September.

*Size.*—Smaller than fruit of St. Julien A; axial diameter 15.5 mm (14–17 mm); transverse diameter 16 mm (14–18 mm).

*Shape.*—Round, flattened at stalk and eye end.

*Color.*—Deep bluish-purple, with an overall bloom.

*Stalk.*—Length 8 mm (7.5–8.5 mm).

General Characteristics

Suckering: Rare, as with most dwarf rootstocks.

Size control potential: Plum trees worked on the Pixy variety are expected to attain two thirds the size of those on St. Julien A rootstock.

Yield potential: Plum varieties worked on Pixy variety give higher proportion of fruit relative to wood than when worked on St. Julien A rootstock.

Root bark ratio: Victoria worked on Pixy variety shows a higher root bark percentage than a comparable tree on St. Julien A rootstock.

Induction of precocious fruiting in scion varieties: The Pixy variety appears to induce fruit bud formation early in the life of the worked tree, and produces heavier crops per unit area than St. Julien A rootstock.

I claim:

1. A new and distinct variety of plum tree useful as a dwarfing rootstock selected from seedlings of *Prunus insititia* St. Julien d'Orleans types substantially as illustrated and described which when used as a plum understock induces less growth of the plum tree, and a higher cropping efficiency on the scion.

* * * * *